United States Patent [19]

Takagi et al.

[11] Patent Number: 5,116,815
[45] Date of Patent: May 26, 1992

[54] PF 1022 SUBSTANCE, METHOD OF TREATING HELMINTHIC PARASITIC INFECTION AND ANTHELMINTIC COMPOSITION

[75] Inventors: Masayuki Takagi; Tadaaki Okada; Naotoshi Akai; Takashi Yaguchi; Shinji Miyadoh; Takashi Shomura; Toru Sasaki; Masaji Sezaki; Takao Shimizu; Masashi Niida, all of Kanagawa, Japan

[73] Assignee: Meiji Seika Kaisha Ltd., Tokyo, Japan

[21] Appl. No.: 475,544

[22] Filed: Feb. 6, 1990

[30] Foreign Application Priority Data

Feb. 7, 1989 [JP] Japan .................................. 1-26739

[51] Int. Cl.⁵ ...................... A61K 37/02; C07K 7/54; C07K 11/02
[52] U.S. Cl. ..................................... 514/11; 530/323; 530/317; 424/122; 435/71.1; 930/270; 930/DIG. 536
[58] Field of Search ................... 530/317, 323; 514/11; 424/122

[56] References Cited

U.S. PATENT DOCUMENTS 4,456,592 6/1984 Okumura et al. .................... 530/317

OTHER PUBLICATIONS

Bassianolide, a New Insecticidal Cyclodepsipeptide from *Beauveria bassiana* and *Verticillium iecanii* (Masaharu Kanaoka, Akira Isogai, Shigeo Murakoshi, Masakatsu Ichinoe, Akinori Suzuki and Saburo Tamura, Agric. Biol. Chem., 42 (3), 629-635, 1978).

Chemical and Pharmaceutical Bulletin, vol. 36, No. 8, 1988, pp. 3199-3201; H. Kataoka et al.: "Selective Transport ... Liquid Membrane".

Chemical Abstracts, vol. 105, No. 5, Aug. 4, 1986; Columbus, Ohio, USA T. Katagi et al.: "Synthesis of ... L-amino acid. II" p. 789; ref. no. 43294C.

Chemical Abstracts, vol. 97, No. 23, Dec. 6, 1982, Columbus, Ohio, USA, T. Katagi et al.: "Syntheses of ... L-amino acids" p. 611; ref. No. 198526V & Heterocycles 1982.

Tetrahedron, vol. 43, No. 20, 1987, pp. 4519-4530; H. Kataoka et al.: "Syntheses of ... liquid membrane".

Primary Examiner—Y. Christina Chan
Attorney, Agent, or Firm—Sughrue, Mion, Zinn, Macpeak & Seas

[57] ABSTRACT

A novel substance having anthelmintic activity, the PF 1022 substance, which is produced by cultivating a fungal strain capable of producing the substance and recovering the substance from the culture.

3 Claims, 4 Drawing Sheets

PF 1022 SUBSTANCE, METHOD OF TREATING HELMINTHIC PARASITIC INFECTION AND ANTHELMINTIC COMPOSITION

FIELD OF THE INVENTION

This invention relates to a novel substance having anthelmintic activity, namely the PF 1022 substance, to a method of producing the same, to an anthelmintic composition containing the same and to a treating and preventing method using the same.

BACKGROUND OF THE INVENTION

Hithertofore, a number of physiologically active substances which microorganisms produce have been known. However, none of them is known to have the physico-chemical properties that are identical to those of the PF 1022 substance according to the invention. It is further known that a number of compounds have anthelmintic activity. However, those substances which are produced by microorganisms and have anthelmintic activity, such as the novel PF 1022 substance of the present invention, are in a very small minority, inclusive of destomycin A, hygromycin B and avermectin.

Also, a substance similar in chemical structure to the substance of the present invention is known as bassianolide (Agric. Biol. Chem., 42(3), 629-635 (1978). However, this substance has no anthelmintic activity.

Parasitic diseases, which are generally caused by parasitic infestation or infection in host animals, cause serious damage to the health of humans and animals and to agriculture. Therefore, the advent of any new anthelmintic is always waited for.

SUMMARY OF THE INVENTION

It is an object of the invention to provide a novel compound having anthelmintic activity.

Another object is to provide an established method of producing the same.

A further object is to provide an anthelmintic composition containing the same as active ingredient as well as a method of treating and preventing parasitic infection using the anthelmintic composition.

In order to achieve the above objects, the present inventors searched patiently for substances having anthelmintic activity. As a result, it was found that the culture of a fungal strain contains an anthelmintic substance. The inventors isolated the active substance and established its physicochemical properties.

Figure 1:
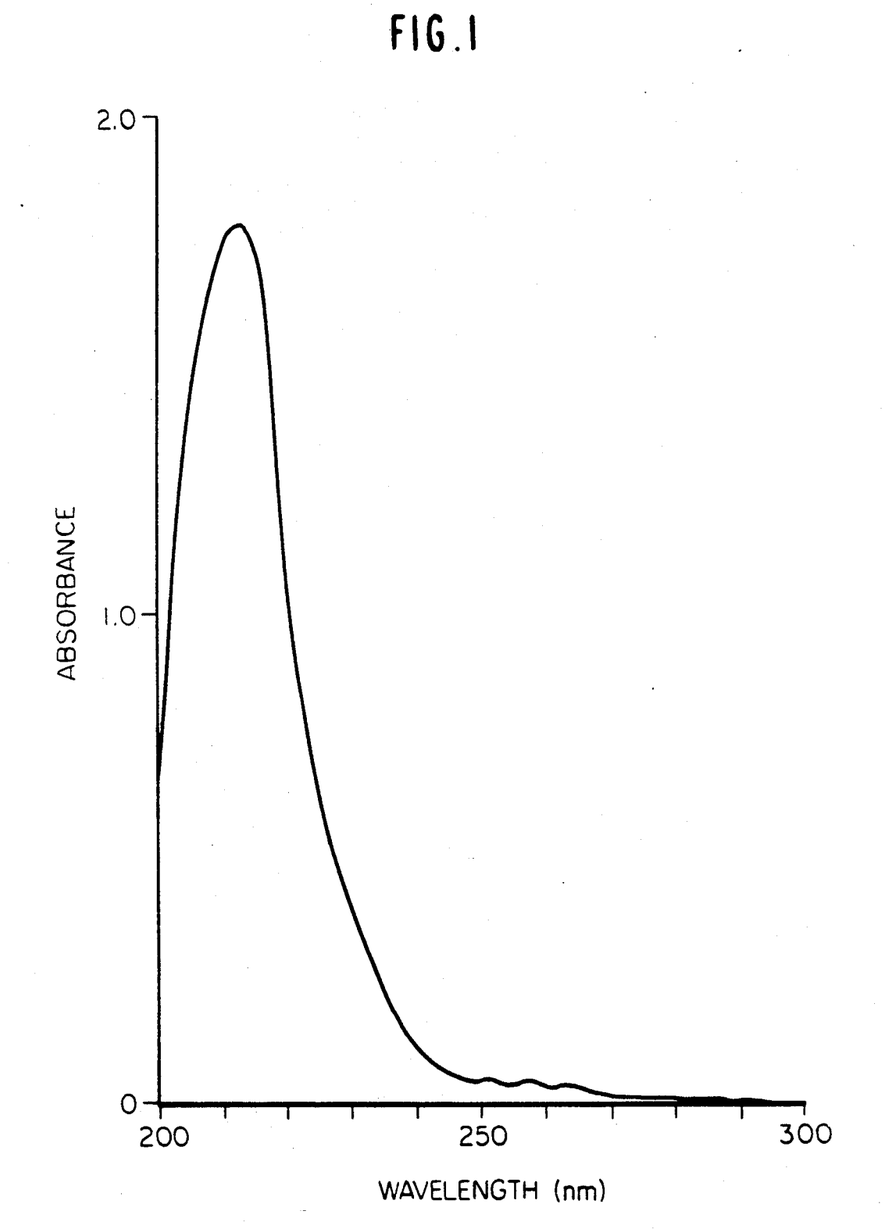
FIG. 1 shows an ultraviolet absorption spectrum of the PF 1022 substance in methanol (100 μg/ml).
Figure 2:
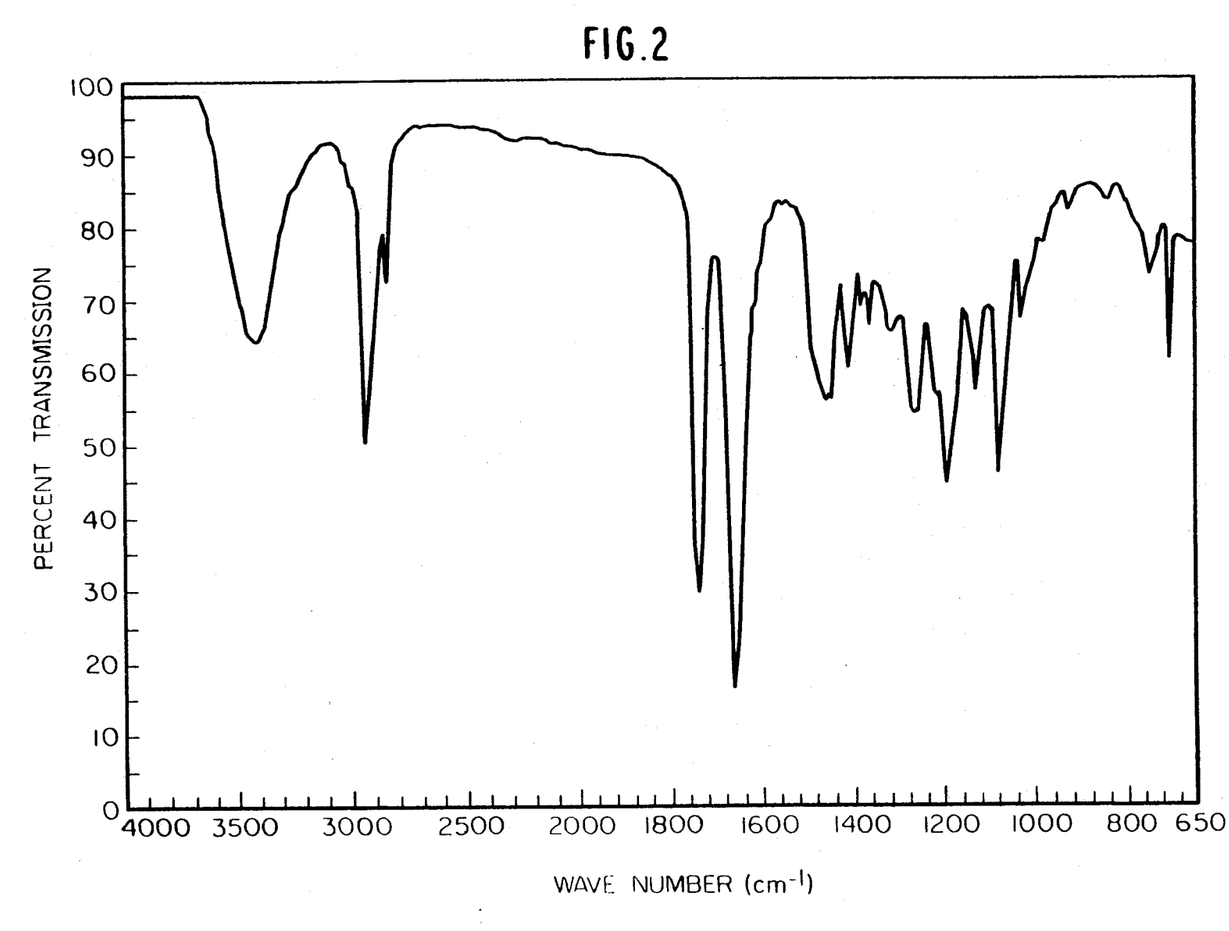
FIG. 2 shows an infrared absorption spectrum of the PF 1022 substance as recorded by the potassium bromide disk method.
Figure 3:
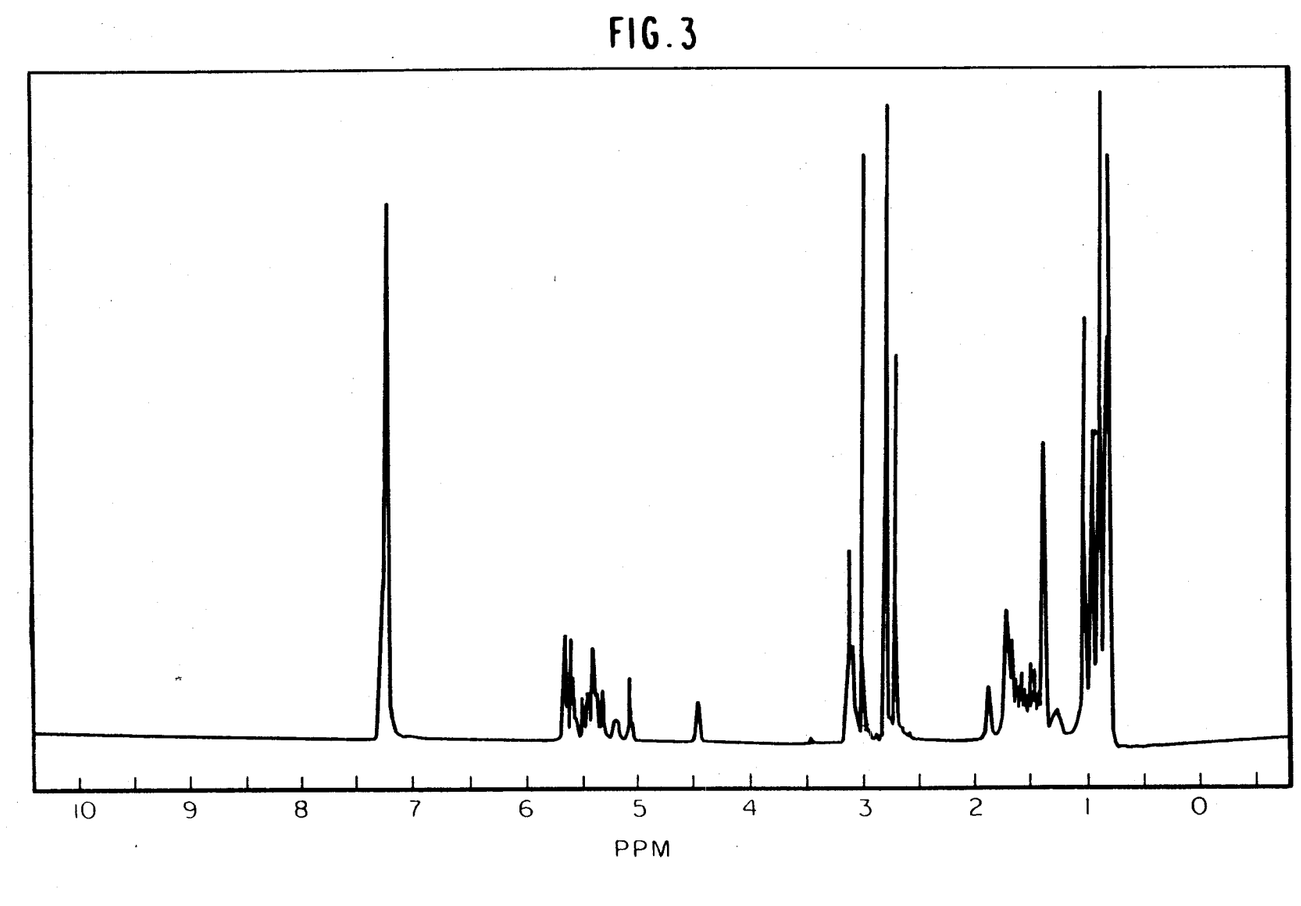
FIG. 3 shows a proton nuclear magnetic reasonance spectrum of the PF 1022 substance as recorded in a deuteriochloroform solution at 400 MHz.
Figure 4:
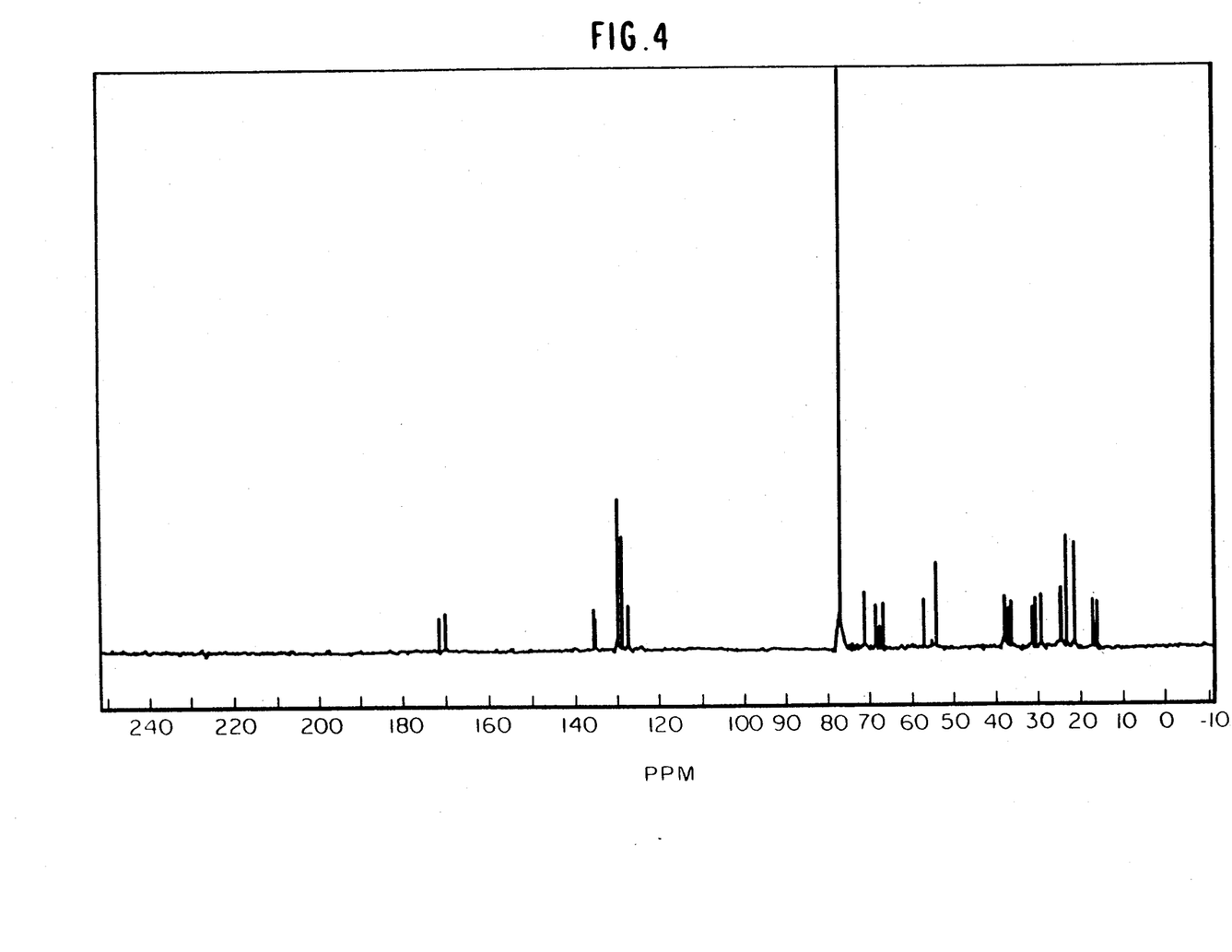
FIG. 4 shows a carbon 13 nuclear magnetic resonance spectrum of the PF 1022 substance as recorded in a deuteriochloroform solution at 100 MHz.

Thus the invention provides, in one aspect thereof, the PF 1022 substance which has the following characteristics:

(1) Appearance: Colorless crystals;
(2) Melting point: 104°-106° C.;
(3) Molecular formula: $C_{52}H_{76}N_4O_{12}$;
(4) Elemental analysis: Calculated (%): C, 65.80; H, 8.07; N, 5.90 Found (%): C, 65.46; H, 8.25; N, 6.10;
(5) Mass spectrum (EI-MS): m/z 948 (M+);
(6) Specific rotation $[\alpha]_D^{22}$: −102° (c=0.1, methanol);
(7) Ultraviolet absorption spectrum: As shown in FIG. 1;
(8) Infrared absorption spectrum: As shown in FIG. 2;
(9) $^1$H NMR spectrum: As shown in FIG. 3;
(10) $^{13}$C NMR spectrum: As shown in FIG. 4;
(11) Solubility: Soluble in methanol, ethyl acetate, acetone, chloroform and dimethyl sulfoxide; insoluble in water;
(12) Classification by basicity, acidity or neutrality: Neutral substance.

X ray analysis data indicate that the PF 1022 substance has the following chemical structure:

In a second aspect, the invention provides a method of producing the PF 1022 substance which comprises cultivating a fungal strain capable of producing the PF 1022 substance and recovering the PF 1022 substance from the culture.

In a further aspect, the invention provides an anthelmintic composition which contains the PF 1022 substance.

DETAILED DESCRIPTION OF THE INVENTION

The strain of microorganism which can produce the PF 1022 substance, namely the strain PF 1022, is a kind of fungus newly isolated from a plant sample collected in Ibaraki Prefecture, Japan in 1988 and has the following mycological properties.

Mycological Properties of the Strain PF 1022

It grows abundantly, at 25° C., on the following four media: potato dextrose agar (PDA), potato carrot agar (PCA), malt extract agar (MEA) and oatmeal agar (OA); white fluffy hyphae covering all over the petri dish (>85 mm) in 7 days. The reverse side of the colony is initially white to light yellow. After about 3 weeks of growing, dark brown spots, 2 to 3 mm in diameter, are observable on said side. Any other particular morphological characteristics, such as conidium formation, are not observable. Soluble pigment formation is insignificant. Good growth is attained within the pH range of 5 to 7.

It grows poorly, at 25° C., on the following media: CZAPEK DOX AGAR (CzA) a medium for observation of morphological characteristics of molds, which contains CZAPEK DOX BROTH consisting of 30 g of saccharose, 3 g of sodium nitrate, 1 g of dipotassium phosphate, 0.5 g of magnesium sulfate, 0.5 g of potassium chloride and 0.01 g of ferrous sulfate, per liter of water (final pH 7.3±21) supplemented with 1.5% agar;, MIURA AGAR (LcA) a medium for observation of morphological characteristics of molds, particularly for sporulation, which contains 1 g of glucose, 1 g of $KH_2PO_4$, 0.2 g of $MgSO_4 \cdot 7H_2O$, 0.2 g of KCl, 2 g of $NaNO_3$, 0.2 g of yeast extract, 13 g of agar, per liter of water (final pH 6.5-7.0); and corn meal agar (CMA); the size of the colony, which is white and fluffy, being about 10 to 20 mm in diameter after 7 days of growing. Conidium formation or the like is not observable. It does not grow at 37° C. At 15° C., it grows on PCA, PDA, MEA and OA to the size of about 35 to 50 mm while, in other respects, the cultural characteristics are nearly the same as those observable at 25° C.

One-month observation at 25° C. following inoculation of plain agar covered with wheat straw, banana leaves, carnation leaves or the like fails to reveal any particular morphological characteristics, such as conidium formation.

In view of the above, this strain was named strain PF 1022 belonging to the order Agonomycetales (*Mycelia sterilia*).

This strain has been deposited with the Fermentation Research Institute, Agency of Industrial Science and Technology, Japan since Jan. 24, 1989 under the deposit number FERM BP-2671 in accordance with the Budapest Treaty.

Like other fungal strains, the stain PF 1022 is labile in its properties. Thus, for instance, any mutant (resulting from spontaneous or artificially induced mutation), phenozygote or genetic recombinant derived from this strain may be used in the practice of the invention if it can produce the PF 1022 substance. In practicing the method of the invention, the above-mentioned fungal strain or any other PF 1022 substance-producing fungal strain is cultivated in a medium containing ordinary nutrients which can be generally utilized by microorganisms. Those nutrient sources that are known in the art to be useful in growing fungi may be used.

Method of Cultivating the Strain PF 1022

Usable as the carbon source are glucose, sucrose, starch syrup, dextrin, starch, glycerol, molasses, and animal and vegetable oils, among others. Usable as the nitrogen sources are, for example, soybean cake, wheat germ, corn steep liquor, cottonseed cake, meat extract, peptone, yeast extract, ammonium sulfate, sodium nitrate and urea. Inorganic salts capable of giving sodium, potassium, calcium, magnesium, cobalt, chloride, phosphate, sulfate and other ions may effectively be added to the medium as necessary. Furthermore, organic and inorganic substances capable of promoting the growth of the fungal strain and the production of the PF 1022 substance may appropriately be added.

The cultivation is suitably carried out under aerobic conditions, in particular in the manner of submerged culture. While the temperature range of 15°-30° C. is suited for the cultivation, the optimal growth temperature is about 26° C. in most instances. In shake culture or tank culture, the production of the PF 1022 substance generally arrives at a maximum accumulation in 2 to 10 days although the period required therefor may vary depending on the medium and culture conditions employed. When the accumulation of the PF 1022 substance is at its peak, the cultivation process is discontinued, and the desired product is isolated and purified from the culture fluid.

Purification of the PF 1022 Substance

The PF 1022 substance produced in the above manner can be recovered from the culture by ordinary means of separation utilizing its physicochemical characteristics, for example, by solvent extraction, ion exchange resin treatment, adsorption or partition column chromatography, gel filtration, dialysis, precipitation and so forth, either alone or in appropriate combination. Thus, for example, the PF 1022 substance can be extracted from the cultured cells with acetone-water or methanol-water. The PF 1022 substance accumulated in the culture supernatant can be adsorbed on the synthetic adsorbent DIAION HP-20 (a porous carrier for chromatography manufactured by Mitsubishi Kasei Corporation), for instance, or can be extracted into a water-immiscible organic solvent, such as butanol or ethyl acetate.

For further purification, the PF 1022 may be subjected to chromatography using an adsorbent such as silica gel (e.g. WAKOGEL C-200, a silica gel carrier for chromatography manufactured by Wako Pure Chemical Industries, Ltd.) or alumina or a gel filtration medium such as SEPHADEX LH-20 (a carrier for gel filtration manufactured by Pharmacia Fine Chemical). Reversed-phase high-performance liquid chromatography is another efficient means for that purpose.

During the purification steps, detection of the PF 1022 substance can be carried out by silica gel thin-layer chromatography or high-performance liquid chromatography. In the case of thin-layer chromatography, a sample is applied to a silica gel plate (e.g. MERCK, ART 5715a silica gel plate for thin-layer chromatography manufactured by Merck Co.) and developed with chloroform-ethyl acetate (2:1 by volume). The PF 1022 substance can be detected as a blue spot at Rf value of 0.57 using a molybdenum reagent as a color-producing reagent. In the case of high-performance liquid chromatography, sample is applied on a column (e.g. ODA-H, a carrier for reverse phase high performance liquid chromatography manufactured by Shimadzu Corporation, 4 mm (i.d.)×150 mm) and developed with a 80% acetonitrile solution at a flow rate of 0.75 ml/min. The PF 1022 substance can be detected as a peak appearing at a retention time of 7.1 min. by measuring the absorbance at 220 nm.

In its third aspect, the invention provides an anthelmintic composition containing the PF 1022 substance as active ingredient.

Animals to which the PF 1022 substance can be applied as an anthelmintic may include, among others, swine, cattle, horses, rabbits, sheep, goats, chickens, ducks, turkeys, mice, rats, guinea pigs, monkeys, dogs, cats, small birds, and the like domestic animals, domestic fowls, experimental animals and pets. The PF 1022 substance can also be applied to humans. Parasites that can be eliminated from host animals with the PF 1022 substance may include, among others, such parasites of cattle and sheep as twisted stomachworms (*Haemonchus contortus*), stomachworms (*Ostertagia ostertagia*), small hairworms belonging to the genus Trichostrongylus (e.g. *T. colubriformis*), those belonging to the genus (*Cooperia curticei*), nodularworms belonging to the genus Oesophagostomum (*Oesophagostomum radiatum, Oesophagostomum columbianum, Oesophagostomum venulosum*), amphistomes (e.g. *Paramphistomum cervi*), intestinal tapeworms (*Moniezia benedeni*), lungworms (*Dictyocaulus filaria, Dictyocaulus viviparus*) and liver flukes (*Fasciola hecatica*), such parasites of swine as large intestinal roundworms (*Ascaris suum*), whipworms (*Trichuris suis*) and nodularworms (*Oesophagostomum dentatum*), such parasites of horses as large roundworms (*Parascaris equorum*), pinworms (*Oxyuris equi*), stomachworms belonging to the genus Habronema (e.g. *Habronema megastoma*), large strongyles belonging to the genus Strongylus (e.g. *S. equinus*), small strongyles belonging to the genus Triodontophorus (e.g. *T. serratus*), such parasites of dogs as roundworms (*Toxocara canis*), hookworms (*Ancylostoma canium*), whipworms (*Trichuris vulpis*) and heart worms (*Dirofilaria immitis*), such parasites of cats as roundworms (*Toxocara cati*) and tapeworms (*Diphyllobothrium erinacei*) and such parasites of chickens as roundworms (*Ascaridia galli*), capillarid worms or hairworms belonging to the genus Capillaria (e.g. *C. annulate*) and cecal worms (*Heterakis gallinae*) as well as such digestive tract parasites in humans as roundworms (*Ascaris lumbricoides*), pinworms (*Enterobius vermicularis*), hookworms (*Ancylostoma duodenale, Ancylostoma ceylanicum, Necator americanus*), oriental hairworms (*Trichostrongylus orientalis*), strongyloides worms (*Strongyloides stercoralis*) and whipworms (*Trichuris trichiura*).

The PF 1022 substance can be used for the treatment and prevention of parasitic infections. For therapeutic treatment, the PF 1022 substance may be administered orally or parenterally. For oral administration, the substance may be administered in the form of a solution in glycerol, polyethylene glycol or the like, suspension or emulsion in oils such as peanut oil, soybean oil or the like, for forced administration by the stomach catheter or the like, in the form of a mixture or dilution with an ordinary feed or potable water, or in the form of ordinary dosage forms suited for oral administration, such as tablets, capsules, pellets, boluses, powders or soft capsules. For parenteral administration, it may be administered subcutaneously, intramuscularly, intravenously, intraperitoneally or by the like route by injection or the like means in the form of water-insoluble preparations in peanut oil, soybean oil or the like or in the form of water-soluble preparations in glycerol, polyethylene glycol or the like. For prophylactic purposes, the substance is generally administered orally in admixture with a feed in ordinary use. In the case of prophylactic use, the duration of administration is not limited but, in most instances, a duration of about 2 months is sufficient for broiler chickens or the like and a duration of five months for swine.

The dose of the PF 1022 substance may vary depending on the animal to be treated, the parasite or parasites and the method of administration. For instance, when chicken roundworms are to be eliminated by oral administration of a liquid preparation using a stomach catheter, the dose is not less than 0.05 mg/kg, preferably 0.2 to 3 mg/kg, once or 2 to 5 times per day. For preventive purposes, the substance is added to a feed in a concentration of not less than 1 ppm/feed, preferably 5 to 10 ppm/feed, once or 2 to 5 times per day and administered continuously.

Furthermore, a solution or suspension of the PF 1022 substance in a liquid carrier may be administered parenterally to animals by subcutaneous or intramuscular injection, for instance. Nonaqueous formulations in which vegetable oils, such as peanut oil and soybean oil, are used as well as aqueous parenteral formulations which contain water-soluble excipients, such as glycerol and polyethylene glycol, may be used for parenteral administration. These formulations generally contain the PF 1022 substance in an amount of 0.1 to 10% by weight. The daily parenteral dose is generally not less than 0.01 mg/kg, preferably within the range of 0.1 to 10 mg/kg.

Even when the PF 1022 substance is orally administered to mice at the dose of 300 mg/kg, normal body weight gains are obtained without any abnormalities. This indicates that this substance has very low toxicity. The PF 1022 substance gives negative results in the Ames test and mammalian cell chromosomal aberration test and it has thus been demonstrated that there are no mutagenicity problems.

The following examples are given only for the purpose of illustrating the invention and are by no means limitative of the scope of the invention. It is a matter of course that various modifications and variations may be made without departing form the spirit of the invention.

EXAMPLE 1

A medium having the following composition was used as the seed culture medium: 1.0% starch, 1.0% glucose, 0.5% cottonseed cake, 0.5% wheat germ, 0.5% soybean cake, 0.5% yeast extract, 0.1% magnesium sulfate (heptahydrate), 0.2% calcium carbonate and 0.2% sodium chloride.

The production medium used had the following composition: 3.0% starch syrup, 1.0% soybean oil, 0.8% wheat germ, 1.0% soybean cake, 1.0% dried yeast, 0.3% calcium carbonate, 0.2% magnesium sulfate (heptahydrate) and 0.2% sodium chloride.

The media were always adjusted to pH 7.0 prior to sterilization.

The seed culture medium mentioned above was distributed in 20-ml portions into 100-ml erlenmeyer flasks, sterilized at 120° C. for 15 minutes and inoculated with 2 to 3 loopfuls per flask of a slant agar culture of the imperfect fungus strain PF 1022 (FERM BP-2671). Shake culture was conducted at 26° C. for 7 days to give a primary seed culture. Then, the seed culture medium was distributed in 80-ml portions into 500-ml erlenmeyer flasks, sterilized at 120° C. for 15 minutes and inoculated with 4 ml per flask of the above-mentioned primary seed culture. Shake culture was performed at 26° C. for 2 days to give a secondary seed culture. The production medium was distributed in 35-liter portions into two 50-liter jar fermentors, sterilized at 120° C. for 30 minutes and inoculated with the above-mentioned secondary seed culture (the sum total from five 500-ml flasks per fermentor). Cultivation was carried out at 26° C. for 5 days with aeration (20 l/minute) and stirring (250 rpm for the first 65 hours; thereafter, 400 rpm).

After completion of cultivation, diatomaceous earth (filter aid) was added to the culture and the mixture was filtered. To the cell-containing solid matter thus obtained was added 60% acetone-water (62 l). The mixture was stirred for 1 hour and the cells were then filtered off. The acetone was distilled off from the thus-obtained cell extract to give a concentrate (11.7 l). The PF 1022 substance was extracted from this concentrate with ethyl acetate (23 Concentration of the ethyl acetate layer gave an oily substance (19.8 g). This oily substance was subjected to column chromatography using silica gel (WAKOGEL C 200, 250 g) with chloroform (2 l) and a mixed solvent composed of chloroform and methanol (100:1, 1.5 l) as the developing solvent. Detection of the PF 1022 substance was carried out by silica gel thin-layer chromatography using a silica gel TLC plate (MERCK, ART. 5715), a mixed solvent of chloroform and ethyl acetate (2:1 by volume) as a developing solvent and a molybdenum reagent as a color-producing reagent. The PF 1022 was detected as a blue spot at Rf value of 0.57. The PF 1022 substance-containing fractions were combined and concentrated to dryness to give a brown oil (4.25 g). The thus-obtained crude PF 1022 substance was dissolved in a small amount of methanol and subjected to column chromatography using a SEPHADEX ® LH-20 (1 l) column previously equilibrated with methanol and methanol as the developing solvent. The PF 1022 substance-containing fractions were combined and concentrated to dryness to give a light-yellow powder (594 mg). A 100-mg portion of this powder was purified by high performance liquid chromatography (YMC, D-ODS-5, (ODS: *Octadecyl silica*): a carrier for reverse phase high performance liquid chromatography manufactured by Yamamura Chemical) using a mixed solvent composed of acetonitrile and water (85:15) as the developing solvent. The PF 1022 substance-containing fractions were combined and the solvent was distilled off to give a colorless powder (65.5 mg). This powder was dissolved in 0.5 ml of acetone, 5 ml of hexane was added to the solution, and the mixture was allowed to stand overnight at room temperature. The PF 1022 substance was obtained as colorless pillars (24.9 mg). The thus-obtained PF 1022 substance was used in the following Examples.

EXAMPLE 2

Chickens verified to be artificially infected with large intestinal roundworms (*Ascaridia galli*) by scatoscopy were used in groups of three animals. The PF 1022 substance was used at five levels of dose from 0.2 mg/kg to 3 mg/kg. A total of 18 chickens were used in 6 groups, inclusive of an untreated control group.

For administration, an amount of the PF 1022 substance exactly equal to the dose calculated on the basis of the body weight of each chicken was weighed and suspended in water containing carboxymethylcellulose (CMC), and the suspension was administered orally as a single dose using a stomach tube. After administration, the worms eliminated were counted daily for each chicken and, after 7 days, each chicken was sacrificed and autopsied and the worms remaining in the intestinal tract were counted. The percent elimination was calculated as follows:

$$\% \text{ Elimination} = \frac{\text{Number of worms eliminated during 7 days}}{\text{Number of worms eliminated during 7 days} + \text{Number of worms remaining}} \times 100$$

Furthermore, the body weight just prior to administration and the body weight after 7 days were measured for each chicken and the percent body weight gain was calculated as follows:

$$\% \text{ Body weight gain} = \frac{\text{Body weight after 7 days of administration} - \text{Body weight before administration}}{\text{Body weight before administration}} \times 100$$

The results of the above test are shown in Table 1.

TABLE 1

Chicken large intestinal roundworm elimination test with PF 1022 substance

| Chicken No. | Dose mg/kg | % Elimination | Mean % Elimination | % Body weight gain | Mean % body weight gain |
|---|---|---|---|---|---|
| 1 |   | 0 |   | 9.5 |   |
| 2 | 0 | 0 | 0 | 8.8 | 9.6 |
| 3 |   | 0 |   | 10.4 |   |
| 4 |   | 12.9 |   | 6.3 |   |
| 5 | 0.2 | 16.0 | 18.5 | 8.4 | 9.6 |
| 6 |   | 26.7 |   | 14.0 |   |
| 7 |   | 16.4 |   | 8.2 |   |
| 8 | 0.5 | 52.1 | 45.4 | 11.5 | 9.2 |
| 9 |   | 67.7 |   | 7.8 |   |
| 10 |   | 60.0 |   | 8.2 |   |
| 11 | 1 | 76.1 | 74.1 | 6.6 | 8.7 |
| 12 |   | 86.2 |   | 11.2 |   |
| 13 |   | 82.1 |   | 7.8 |   |
| 14 | 2 | 93.5 | 84.6 | 10.5 | 8.9 |
| 15 |   | 78.3 |   | 8.4 |   |
| 16 |   | 100 |   | 11.8 |   |
| 17 | 3 | 95.5 | 98.0 | 9.7 | 9.9 |
| 18 |   | 98.3 |   | 8.3 |   |

As shown in Table 1, the PF 1022 substance exhibited anthelmintic activity at the dose of 0.2 mg/kg and the anthelmintic effect increased with the increasing dose, attaining approximately 100% at 3 mg/kg. At the dose giving 100% elimination, the percent body weight gain was comparable to that in the undosed control, indicating that this substance is a very highly safe substance.

EXAMPLE 3

The anthelmintic effect of the PF 1022 substance in swine was evaluated by orally administering the substance to swine found to be infected with large intestinal roundworms (*Ascaris suum*) by scatoscopy.

The PF 1022 substance was administered either once at 5 mg/kg or 10 mg/kg, or at a daily dose of 1.25 mg/kg, 2.5 mg/kg or 5 mg/kg once daily for consecutive 2 days by admixing an amount of the substance as such equal to each dose with a small portion of the ordinary feed. After administration, the worms eliminated were counted and the feces examined for the number of roundworm eggs per gram of feces (EPG) daily. One week after commencement of administration, the animals were sacrificed and autopsied for counting the worms remaining in the intestinal tract.

The results obtained are shown in Table 2.

TABLE 2

Anthelmintic activity of PF 1022 substance against swine large intestinal roundworms

| Number of administrations | Dose (mg/kg/administration) | EPG Before aministration | EPG Upon autopsy | Number of worms eliminated | Number of remaining worms | % Elimination |
|---|---|---|---|---|---|---|
| 1 | 10 | 2100 | 200 | 7 | 5 | 58.3 |
|   | 5 | 99000 | 8000 | 12 | 13 | 48.0 |
| 2 | 5 | 2700 | 0 | 13 | 0 | 100 |
|   | 2.5 | 3300 | 0 | 3 | 1 | 75.0 |
|   | 2.5 | 3800 | 0 | 1 | 1 | 50.0 |
|   | 1.25 | 2300 | 500 | 2 | 9 | 18.2 |
|   | 1.25 | 1800 | 100 | 2 | 4 | 33.3 |

As Shown in Table 2, the substance showed anthelmintic activity already at 1.25 mg/kg when administered for 2 days. The percent worm elimination was not less than 50% in 2 day administration at 2.5 mg/kg and in single administration at 5 mg/kg or 10 mg/kg. Two day administration at 5 mg/kg gave 100% worm elimination.

The PF 1022 substance thus produced a powerful anthelmintic effect against swine large intestinal roundworms.

EXAMPLE 4

The PF 1022 substance was evaluated for its anthelmintic effect on swine whipworms by orally administering it to swine found to be infected with whipworms (*Trichuris suis*) by scatoscopy.

The PF 1022 substance was administered either once at 1 mg/kg, 5 mg/kg or 10 mg/kg, or at a daily dose of 2.5 mg/kg or 5 mg/kg once daily for 2 consecutive days by admixing an amount of the substance as such equal to each dose with a small portion of the ordinary feed. After administration, the number of whipworm eggs in the feces of each animal was determined daily in terms of EPG. In three animals, the worms eliminated were counted as well. One week after initiation of administration, all the animals were sacrificed and autopsied and the worms remaining in the intestinal tract were counted.

The results obtained are shown in Table 3.

TABLE 3

Anthelmintic activity of PF 1022 substance against swine whipworms

| Number of administrations | Dose (mg/kg/administration) | EPG Before aministration | EPG Upon autopsy | Number of worms eliminated | Number of remaining worms | % Elimination |
|---|---|---|---|---|---|---|
| 1 | 10 | 1800 | 0 | —* | 0 | 100 |
|   | 5 | 1500 | 0 | — | 0 | 100 |
|   | 5 | 21600 | 100 | 348 | 14 | 96.1 |
|   | 5 | 3200 | 0 | 90 | 24 | 78.8 |
|   | 1 | 5500 | 1200 | 14 | 334 | 4.0 |
| 2 | 5 | 100 | 0 | — | 0 | 100 |
|   | 2.5 | 2100 | 0 | — | 0 | 100 |
|   | 2.5 | 3000 | 0 | — | 1 | — |

*No data available

As shown in Table 3, the substance showed slight anthelmintic activity when administered once at 1 mg/kg. When administered once at 5 mg/kg, it gave a worm elimination of about 80% to 100%. When it was administered once at 10 mg/kg or for 2 days at 5 mg/kg, no worms were remaining in the animals, with an elimination of 100%. When it was given for 2 days at 2.5 mg/kg, one worm was found remaining in one animal and none in the other animal.

It was thus found that the PF substance has a potent anthelmintic effect on swine whipworms.

EXAMPLE 5

The PF 1022 substance was evaluated for its anthelmintic effect on feline roundworms (*Toxocara cati*) by orally administering the substance once to 12 cats found to be infected with the roundworms by scatoscopy.

The infected cats were used in three groups of 4 animals and given 0.2 mg/kg, 1 mg/kg and 5 mg/kg of the substance, respectively, admixed as such with a small portion of ordinary feed. The observation items were the number of roundworms eliminated during the 7 day observation period following administration and the number of remaining roundworms as found upon autopsy performed 7 days after administration.

The results are shown in Table 4.

TABLE 4

Anthelmintic activity of PF 1022 substance against cat large intestinal roundworms

| Dose (mg/kg) | Number of worms eliminated | Number of remaining worms | % Elimination |
|---|---|---|---|
| 5 | 2 | 0 | 100 |
| 5 | 2 | 0 | 100 |
| 5 | 2 | 0 | 100 |
| 5 | 15 | 0 | 100 |
| 1 | 4 | 0 | 100 |
| 1 | 3 | 0 | 100 |
| 1 | 28 | 0 | 100 |
| 1 | 4 | 1 | 80.0 |
| 0.2 | 2 | 0 | 100 |
| 0.2 | 7 | 0 | 100 |
| 0.2 | 4 | 0 | 100 |
| 0.2 | 1 | 1 | 50.0 |

As shown in Table 4, at 0.2 mg/kg, the elimination was 100% in 3 of 4 animals. At 5 mg/kg, the elimination was 100% in all animals.

The PF 1022 substance was thus found to have a potent anthelmintic effect on feline roundworms.

EXAMPLE 6

The PF 1022 substance was evaluated for its anthelmintic effect on feline hookworms (*Ancylostoma tubaeforme*) by orally administering the substance once to 12 cats found to be infected with said worms by scatoscopy.

The infected cats were divided into three groups of 4 animals and respectively given 0.2 mg/kg, 1 mg/kg and 5 mg/kg of the substance admixed as such with a small portion of the ordinary feed. The observation items were the number of worms eliminated during 7 days following administration and the number of remaining worms found upon autopsy 7 days after administration.

The results are shown in Table 5.

TABLE 5

Anthelmintic activity of PF 1022 substance against cat hookworms

| Dose (mg/kg) | Number of worms eliminated | Number of remaining worms | % Elimination |
|---|---|---|---|
| 5 | 7 | 0 | 100 |
| 5 | 6 | 0 | 100 |
| 5 | 3 | 0 | 100 |
| 5 | 68 | 0 | 100 |
| 1 | 5 | 3 | 62.5 |
| 1 | 10 | 0 | 100 |
| 1 | 56 | 8 | 87.5 |
| 1 | 55 | 1 | 98.2 |
| 0.2 | 82 | 55 | 59.9 |
| 0.2 | 3 | 3 | 50.0 |
| 0.2 | 110 | 240 | 31.4 |
| 0.2 | 6 | 0 | 100 |

As shown in Table 5, at 0.2 mg/kg, the elimination was 100% in one animal. The percent elimination increased with the increasing dose and, at 5 mg/kg, the elimination was 100% in all animals.

It was thus demonstrated that the PF 1022 substance has a potent anthelmintic effect on feline hookworms.

EXAMPLE 7

The PF 1022 substance was evaluated for its anthelmintic effect in sheep mixedly infected with fourth stomachworms (*Ostertaqia circumcincta*) and small intestinal hairworms (*Trichostrongylus colubriformis*) by administering it orally to 24 sheep artificially infected with said two worm species.

The infected sheep were divided into 4 groups of 6 animals, which were respectively given 1 mg/kg, 5 mg/kg, 10 mg/kg and 0 mg/kg (control) of the substance suspended in 0.5% CMC, via a stomach catheter. The observation items were the number of parasite eggs per gram of feces (EPG) before administration, the EPG 7 days after administration, and the number of worms remaining in the fourth stomach and that of worms remaining in the intestinal tract as found upon autopsy 7 days after administration.

The results are shown in Table 6. Each numerical value given is the mean of 6 animals.

TABLE 6

Anthelmintic effects of PF 1022 substance on sheep digestive tract nematodes

| Dose (mg/kg) | EPG | | Number of worms remaining in | |
|---|---|---|---|---|
| | Before administration | At autopsy | Before administration | At autopsy |
| 10 | 2332 | 1970 | 2463 | 5333 |
| 5 | 2458 | 2462 | 4717 | 8317 |
| 1 | 2447 | 3114 | 4967 | 8750 |
| 0 | 2148 | 3103 | 5433 | 10450 |

As shown in Table 6, in the 10 mg/kg group, the number of worms remaining in the fourth stomach and that of worms remaining in the intestinal tract were about half the respective numbers in the control infected group.

The PF 1022 substance was thus found to have an anthelmintic effect on the stomachworms and the hairworms.

EXAMPLE 8

The PF 1022 substance was evaluated for its anthelmintic effect on the so-called digestive tract nematodes parasitizing cattle by orally administering it to three head of cattle found to be infected with such nematodes (*Haemonchus controtus, Ostertaqia ostertagi*, hairworms, cooperids, etc.) by scatoscopy.

The PF 1022 substance was administered either once at 5 mg/kg or for 2 days once daily at 12.5 mg/kg, in the form of a suspension in water, using a stomach catheter. Parasite eggs in feces (EPG) were counted daily for 3 days before administration and for 7 days following administration.

The results are shown in Table 7.

TABLE 7

Anthelmintic effect of PF 1022 substance on bovine digestive tract nematodes

| Dose (mg/kg) | Change in EPG from Day −3 to Day 7 | | | | | | | | | | |
|---|---|---|---|---|---|---|---|---|---|---|---|
| | −3 | −2 | −1 | 0* | 1 | 2 | 3 | 4 | 5 | 6 | 7 |
| 5.0 × 1 | 30 | 32 | 34 | 34 | 44 | 61 | 18 | 30 | 6 | 27 | 7 |
| 12.5 × 2 | 91 | 109 | 109 | 112 | 80 | 26 | 34 | 41 | 41 | 42 | 49 |
| 12.5 × 2 | 58 | 58 | 67 | 64 | 39 | 30 | 41 | 29 | 34 | 40 | 36 |

*Day 0 = day of first administration

As shown in Table 7, at 5 mg/kg, the EPG showed a tendency toward gradual decrease although the data varied fairly widely. After 2 day administration at 12.5 mg/kg, the EPG on the day after the second day of administration was about half that found before administration.

The PF 1022 substance was thus found to have an anthelmintic effect on digestive tract nematodes.

EXAMPLE 9

The PF 1022 substance was evaluated for its anthelmintic effect in a horse found by scatoscopy to be infected with roundworms (*Parascaris equorum*) and strongyles (Strongylus spp.) by orally administering the substance thereto.

The PF 1022 substance was suspended in water and administered with a stomach catheter at 5 mg/kg on the first day and at 2.5 mg/kg on the second day. For both the roundworms and strongyles, parasite eggs in each gram of feces (EPG) as well as parasites eliminated were counted daily for one week following the first administration. For strongyles, the number of worms in 100 g of feces was determined.

The results obtained are shown in Table 8.

TABLE 8

| Anthelmintic effect of PF 1022 substance on equine roundworms and strongyles | | | | | | | | |
|---|---|---|---|---|---|---|---|---|
| | Day | | | | | | | |
| | 0 | 1 | 2 | 3 | 4 | 5 | 6 | 7 |
| Dose (mg/kg) | 5 | 2.5 | — | — | — | — | — | — |
| Equine roundworms | | | | | | | | |
| EPG | 77 | 52 | 0.4 | 0.2 | 0 | 0 | 0.2 | 0 |
| Number of worms eliminated | 0 | 22 | 17 | 0 | 0 | 0 | 0 | 0 |
| Strongyles | | | | | | | | |
| EPG | 265 | 82 | 0.6 | 0.4 | 0 | 0 | 0.2 | — |
| Number of worms eliminated | 0 | 82 | 0 | 0 | 0 | 0 | 0 | 0 |

Notes:
*: Number per 100 g feces.
—: No administration

As shown in Table 8, the EPG began to decrease on the second day of administration and showed a drastic decrease on the next day. Roundworm elimination was observed on the second day of administration and on the next day. No roundworm elimination was found on the subsequent days. Strongyle elimination was found only on the second day of administration (82 worms per 100 g of feces). No strongyles were eliminated on the subsequent days.

It was thus demonstrated that the PF 1022 substance has a strong anthelmintic effect on equine roundworms and strongyles.

EXAMPLE 10

The PF 1022 substance was evaluated for its anthelmintic effect on 9 chickens found, by scatoscopy, to be infected with large intestinal roundworms (*Ascaridia galli*) by administering it in admixture with the feed.

The chickens were divided into three groups of 3 animals, which served as the 1 ppm, 5 ppm and 10 ppm groups. The feed containing the PF 1022 substance in each concentration mentioned above was given to the chickens for 3 weeks. Parasite eggs in feces were counted at one-week intervals in terms of EPG and worms eliminated were counted daily. At the end of the administration period, the chickens were sacrificed and autopsied and the worms remaining therein were counted.

The results obtained are shown in Table 9.

TABLE 9

| Anthelmintic activity of PF 1022 substance against chicken large intestinal roundworms | | | | | |
|---|---|---|---|---|---|
| Concentration in feed (ppm) | Number of eggs before starting administration | EPG after 2 weeks | Number of worms eliminated | Number of worms remaining | % Elimination |
| 10 | 300 | 0 | 44 | 0 | 100 |
| 10 | 300< | 0 | 55 | 0 | 100 |
| 10 | 176 | 2 | 45 | 55 | 46.5 |
| 5 | 300 | 0 | 68 | 11 | 86.1 |
| 5 | 300< | 0 | 29 | 23 | 56.9 |
| 5 | 158 | 0 | 60 | 36 | 62.5 |
| 1 | 300< | 131 | 6 | 49 | 10.9 |
| 1 | 300< | 79 | 4 | 96 | 4.0 |
| 1 | 172 | 272 | 0 | 83 | 0 |

As shown in Table 9, in the 1 ppm group, parasite elimination was observed only in 2 animals. In the 5 ppm group, the number of eggs in feces was zero in all animals at 2 weeks after the initial administration while there were some parasites remaining in the animals. In the 10 ppm group, the parasite elimination was 100% in 2 of the animals.

It was thus found that the PF 1022 substance has a potent anthelmintic effect on chicken large intestinal roundworms.

EXAMPLE 11

The PF 1022 substance was evaluated for its anthelmintic activity by adding it to test tubes in which bovine twisted stomach worms (*Haemonchus contortus*) isolated from the bovine fourth stomach were swimming.

A physiological salt solution was distributed into 4 test tubes and warmed to 39°–40° C. Three to five twisted stomachworms collected from the bovine fourth stomach were put into the medium in each test tube and allowed to swim therein. An appropriate amount of the PF 1022 substance was dissolved in a small amount of dimethyl sulfoxide and the solution was added dropwise to the medium and, after stirring for admixing, the behavior of each worm was observed. The amount of the PF 1022 substance was adjusted so that the final concentrations in the culture medium in three tubes amounted to 2 ppm, 8 ppm and 40 ppm, respectively. Dimethyl sulfoxide alone was added dropwise to the remaining test tube, which served as a control.

The worms stopped moving in 10 minutes at the PF 1022 substance concentration of 40 ppm, in 15 minutes at 8 ppm, and in 25 minutes at 2 ppm. In the control tube (where dimethyl sulfoxide alone was added dropwise), the movement of the worms became weakened but motility was still observed even after the lapse of 1 hour.

It was thus revealed that the PF 1022 substance has a potent paralyzing activity against the twisted stomachworm.

EXAMPLE 12

The PF 1022 substance was evaluated for its anthelmintic effect in dogs by orally administering it to dogs found to be infected with roundworms (*Toxocara canis*), hookworms (*Ancylostoma caninum*) and whipworms (*Trichuris vulpis*l), respectively, by scatoscopy.

The substance was orally administered once at the dose of 5 mg/kg to a dog infected with the roundworms or hookworms by admixing the substance with a small portion of the ordinary feed, and the worms eliminated and those remaining in the dog during 7 days following administration were counted.

As a result, six roundworms were eliminated while no roundworms were found remaining in the dog. Twelve hookworms were eliminated while no hookworms were found remaining. Thus, the elimination was 100% in both cases. On the other hand, one of two dogs infected with the above-mentioned whipworms was given orally one single dose of 5 mg/kg and the other 10 mg/kg, and the worms eliminated and those remaining uneliminated during 7 days following administration were counted. At 5 mg/kg, 327 whipworms were eliminated while 504 whipworms were found remaining; the percent elimination was thus 39.4%. At 10 mg/kg, 22 whipworms were eliminated while none were found remaining unieliminated. Thus, the elimination was 100%.

The data mentioned above indicate that the PF 1022 substance has a potent anthelmintic effect on canine roundworms, hookworms and whipworms.

While the invention has been described in detail and with reference to specific embodiments thereof, it will be apparent to one skilled in the art that various changes and modifications can be made therein without departing from the spirit and scope thereof.

What is claimed is:

1. A substance represented by the formula:

wherein said substance has the following characteristics:

(1) Appearance: Colorless crystals;
(2) Melting point: 104°–106° C.;
(3) Molecular formula: $C_{52}H_{76}N_4O_{12}$;
(4l) elemental analysis: Calculated (%): C, 65.80; H, 8.07; N, 5.90; Found (%): C, 65.46; H, 8.25; N, 6.10;
(5) Mass spectrum (EI-MS): m/z 948 (M+);
(6l) Specific rotation $[\alpha]_D^{22}$: $-102°$ (c=0.1, methanol);
(7) Ultraviolet absorption spectrum: As shown in FIG. 1;
(8l) Infrared absorption spectrum: As shown in FIG. 2;
(9) $^1H$ NMR spectrum: As shown in FIG. 3;
(10) $^{13}C$ NMR spectrum: As shown in FIG. 4;
(11) solubility: Soluble in methanol, ethyl acetate, acetone, chloroform and dimethyl sulfoxide; insoluble in water
(12) Classification by basicity, acidity or neutrality: Neutral substance.

2. An anthelmintic composition containing a biologically effective amount of the substance of claim 1 as an active ingredient and a carrier therefor.

3. A method of treating helminthic parasitic infection which comprises administering to animals including humans suffering from helminthic parasitic infection a treating effective amount of the substance of claim 1.

* * * * *